(12) United States Patent
Asami et al.

(10) Patent No.: US 9,074,968 B2
(45) Date of Patent: Jul. 7, 2015

(54) EXHAUST GAS SAMPLING APPARATUS

(71) Applicant: HORIBA, Ltd., Kyoto (JP)

(72) Inventors: Tetsuji Asami, Kyoto (JP); Akihiro Nishimoto, Kyoto (JP); Yosuke Hisamori, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 14/169,210

(22) Filed: Jan. 31, 2014

(65) Prior Publication Data

US 2014/0216132 A1     Aug. 7, 2014

(30) Foreign Application Priority Data

Feb. 6, 2013   (JP) ................. 2013-021808

(51) Int. Cl.
*G01N 7/00* (2006.01)
*G01N 1/22* (2006.01)

(52) U.S. Cl.
CPC ...... *G01N 1/2252* (2013.01); *G01N 2001/2255* (2013.01); *G01N 2001/225* (2013.01)

(58) Field of Classification Search
CPC ................. G01K 2205/04; G01N 2001/2255
See application file for complete search history.

(56) References Cited

U.S. PATENT DOCUMENTS

| 5,218,857 A | 6/1993 | Decker et al. |
| 2003/0159496 A1 | 8/2003 | McDonald et al. |

FOREIGN PATENT DOCUMENTS

| EP | 2410326 A2 | 1/2012 |
| EP | 2515095 A1 | 10/2012 |
| JP | 2000-221123 A | 8/2000 |

*Primary Examiner* — Laura Martin
*Assistant Examiner* — Alex Devito
(74) *Attorney, Agent, or Firm* — Brooks Kushman P.C.

(57) ABSTRACT

The present invention is provided with a control device that sets a split flow ratio that is a ratio of the flow rate of the diluted exhaust gas to be sampled through a diluted exhaust gas sampling flow path to a flow rate of a diluted exhaust gas flowing through a CVS, wherein the control device uses the flow rate (QCVS) of the diluted exhaust gas flowing through the CVS or a value (TCVS or PCVS) related to the flow rate (QCVS) of the diluted exhaust gas to set the split flow ratio (Qsamp/QCVS) so as to make a flow velocity (Vfilter) of the diluted exhaust gas flowing into an analytical device equal to a predetermined value.

4 Claims, 6 Drawing Sheets

US 9,074,968 B2

EXHAUST GAS SAMPLING APPARATUS

CROSS-REFERENCE TO RELATED APPLICATION

This application claims priority to JP Application No. 2013-021808, filed Feb. 6, 2013, the disclosure of which is incorporated in its entirety by reference herein.

TECHNICAL FIELD

The present invention relates to an exhaust gas sampling apparatus that samples exhaust gas exhausted from an engine such as a diesel engine mounted in an automobile.

BACKGROUND

As a conventional exhaust gas sampling apparatus, as described in JPA 2000-221123, there is an apparatus of a constant volume dilution sampling type that samples the total amount of exhaust gas, and dilutes the exhaust gas with dilution air to provide a constant known flow rate.

Specifically, this exhaust gas sampling apparatus is provided with: an exhaust gas flow path through which the exhaust gas flows; a dilution gas flow path through which the dilution gas flows; a dilution tunnel that is connected with the flow paths to produce diluted exhaust gas that is a mixture of the exhaust gas and the dilution gas; a constant volume sampling device (CVS device) of a critical flow venturi type, which is provided on a downstream side of the dilution tunnel; and a sampling flow path for sampling part of the diluted exhaust gas flowing through the dilution tunnel to make the sampled diluted exhaust gas pass through a collection filter for PM collection.

Also, this exhaust gas sampling apparatus is, on an upstream side of the CVS device, provided with a heat exchanger for regulating temperature of the diluted exhaust gas to be constant. The heat exchanger regulates the temperature of the diluted exhaust gas flowing into the CVS device to be constant, and makes a diluted exhaust gas flow rate (flow rate of the diluted exhaust gas passing through a critical flow venturi) controlled by the CVS device constant. For this reason, by setting a flow rate (Qsamp) of the diluted exhaust gas to be sampled through the sampling flow path to a constant ratio (split flow ratio) with respect to the diluted exhaust gas flow rate (QCVS) controlled by the CVS device, a flow rate (Qfilter) of the diluted exhaust gas flowing into the collection filter is made constant.

On the other hand, there is an apparatus having a configuration in which in the above-described exhaust gas sampling apparatus, the heat exchanger is not provided on the upstream side of the CVS device. To set the split flow ratio, the exhaust gas sampling apparatus having such a configuration sets a diluted exhaust gas flow rate (QCVS) controlled by a CVS device to a flow rate (Qstandard_state) in a standard state (e.g., 20° C., 1 atm).

Meanwhile, in recent years, a flow velocity (Vfilter) of diluted exhaust gas passing through a collection filter has been limited. For example, in the exhaust gas testing regulations (CFR part 1065) in US, or the like, a limit where the flow velocity (Vfilter) of the diluted exhaust gas passing through the collection filter is 100 cm/s or less and close to the value is provided.

However, in the apparatus having the configuration in which the heat exchanger is not provided on the upstream side of the CVS device, temperature of diluted exhaust gas is increased during exhaust gas sampling, and along with the increase in temperature of the diluted exhaust gas, the flow rate of the diluted exhaust gas passing through the CVS device is reduced. As a result, using the setting flow rate (Qstandard_state) in the standard stat to make the split flow rate constant causes a flow rate (Qfilter) of the diluted exhaust gas passing through a collection filter to be also reduced along with the reduction in diluted exhaust gas flow rate during the exhaust gas sampling. For this reason, there occurs a problem that as the exhaust gas sampling proceeds, a diluted exhaust gas flow velocity (Vfilter) becomes separated from the regulated value.

SUMMARY

Technical Problem

Therefore, the present invention is made in order to solve the above-described problem at once, and a main intended object thereof is to, in an exhaust gas sampling apparatus having a configuration in which a heat exchanger is not provided on an upstream side of a constant volume sampler such as a CVS device, regulate a flow rate or flow velocity of diluted exhaust gas flowing into an analytical device to a predetermined value.

Solution to Problem

That is, an exhaust gas sampling apparatus according to the present invention is provided with: an exhaust gas flow path through which exhaust gas flows; a dilution gas flow path through which dilution gas flows; a main flow path that is connected with the exhaust gas flow path and the dilution gas flow path to flow diluted exhaust gas that is a mixture of the exhaust gas and the dilution gas; a constant volume sampler that is provided in the main flow path; a diluted exhaust gas sampling flow path for sampling part of the diluted exhaust gas from the main flow path to introduce the part into an analytical device; a flow rate control mechanism that is provided in the diluted exhaust gas sampling flow path to control a flow rate of the diluted exhaust gas to be sampled through the diluted exhaust gas sampling flow path; and a control device that controls the flow rate control mechanism to set a ratio of the flow rate of the diluted exhaust gas to be sampled through the diluted exhaust gas sampling flow path to a flow rate of the diluted exhaust gas flowing through the constant volume sampler, wherein the control device uses the flow rate of the diluted exhaust gas flowing through the constant volume sampler or a value related to the flow rate of the diluted exhaust gas to set the ratio so as to make the flow rate of the diluted exhaust gas flowing into the analytical device equal to a predetermined value.

If so, the flow rate of the diluted exhaust gas flowing through the constant volume sampler, or the value related to the flow rate of the diluted exhaust gas is used to set the flow rate of the diluted exhaust gas to be sampled so as to make the flow rate of the diluted exhaust gas flowing into the analytical device equal to the predetermined value, and therefore the flow rate or a flow velocity of the diluted exhaust gas flowing into the analytical device can be regulated to the predetermined value or a predetermined value.

In addition, the value related to the flow rate of the diluted exhaust gas refers to temperature or pressure of the diluted exhaust gas flowing through the constant volume sampler, or some other value. Also, the temperature of the diluted exhaust gas flowing through the constant volume sampler refers to temperature of the diluted exhaust gas flowing into the constant volume sampler, and is diluted exhaust gas temperature outputted from a temperature sensor provided on an upstream side of the constant volume sampler. Similarly, the pressure of the diluted exhaust gas flowing through the constant volume sampler refers to pressure of the diluted exhaust gas flowing into the constant volume sampler, and is diluted exhaust gas pressure outputted from a pressure sensor provided on the upstream side of the constant volume sampler.

Also, preferably, the control device uses the temperature of the diluted exhaust gas flowing through the constant volume sampler to set the ratio so as to make the flow rate of the diluted exhaust gas flowing into the analytical device equal to the predetermined value.

If so, the temperature of the diluted exhaust gas flowing through the constant volume sampler is used to calculate the flow rate of the diluted exhaust gas flowing through the constant volume sampler, and the flow rate of the diluted exhaust gas is used to set the flow rate of the diluted exhaust gas to be sampled so as to make the flow rate of the diluted exhaust gas flowing into the analytical device equal to the predetermined value, so that in consideration of a temperature-dependent variation in flow rate of the diluted exhaust gas flowing through the constant volume sampler, the flow rate or flow velocity of the diluted exhaust gas flowing into the analytical device can be regulated to the predetermined value.

In addition, to calculate the flow rate of the diluted exhaust gas flowing through the constant volume sampler, preferably, in addition to the temperature of the diluted exhaust gas flowing through the constant volume sampler, the diluted exhaust gas pressure outputted from the pressure sensor provided on the upstream side of the constant volume sampler is used to perform the calculation.

Preferably, the control device sets the ratio at or immediately before a start of sampling the diluted exhaust gas through the diluted exhaust gas sampling flow path.

If so, the flow rate of the diluted exhaust gas flowing into the analytical device at the start of the sampling can be brought as close to the predetermined value such as a regulated value as possible.

Preferably, the control device sets the ratio every time a test mode is switched, or every time a phase provided in each test mode is switched. Here, as the test mode, a test mode provided in exhaust gas test regulations of each country is possible. Also, as the phase provided in each test mode, a phase such as a cold start phase, a hot start phase, or a transient phase from the cold start phase to the hot start phase is possible.

If so, in each test mode or each phase, the flow rate of the diluted exhaust gas flowing into the analytical device at the start of the sampling can be brought as close to the predetermined value such as a regulated value as possible.

Preferably, the diluted exhaust gas sampling flow path has: a plurality of branched flow paths mutually connected in parallel; and a flow path switching mechanism for switching among the branched flow paths such that the diluted exhaust gas flows through one of the plurality of branched flow paths, each of which is provided with an analytical device, and every time the flow path switching mechanism switches among the branched flow paths, the control device sets the ratio.

In this case, it is possible that the control device sets the ratio at the time when or immediately before the flow path switching mechanism switches among the branched flow paths.

If so, the flow rate of the diluted exhaust gas flowing into each of the analytical devices can be brought as close to a predetermined value set for the analytical device, such as a regulated value, as possible.

Note that in the case of: at the start of sampling the diluted exhaust gas toward a first analytical device, calculating the flow rate of the diluted exhaust gas flowing through the constant volume sampler to set a split flow ratio; after the sampling of the diluted exhaust gas, switching to sampling of the diluted exhaust gas toward a next analytical device; and using the first calculated diluted exhaust gas flow rate to set the split flow ratio, it is expected that exhaust gas temperature may be changed at the time. For this reason, at the time of switching to the next analytical device, again calculating the flow rate of the diluted exhaust gas flowing through the constant volume sampler to set the split flow ratio enables the flow rate of the diluted exhaust gas flowing into the next analytical device to be accurately made equal to the predetermined value.

Preferably, the analytical device is a collection filter for collecting particulate matter contained in the diluted exhaust gas.

If so, an exhaust gas sampling apparatus meeting exhaust gas test regulations of recent years can be provided.

Advantageous Effects of Invention

According to the present invention configured as described, in the exhaust gas sampling apparatus having a configuration in which a heat exchanger is not provided on the upstream side of the constant volume sampler, in consideration of a temperature-dependent variation in flow rate of the diluted exhaust gas flowing through the constant volume sampler, the flow rate of the diluted exhaust gas flowing into the analytical device can be regulated to the predetermined value.

DETAILED DESCRIPTION

In the following, one embodiment of an exhaust gas sampling apparatus according to the present invention is described with reference to drawings.

An exhaust gas sampling apparatus 100 according to the present embodiment is one that, with dilution gas, dilutes engine exhaust gas (hereinafter referred to as "exhaust gas"), which is exhausted from a diesel engine mounted in an automobile or the like, to suck the diluted exhaust gas (hereinafter referred to as "diluted exhaust gas") by a constant volume sampler (hereinafter referred to as a "CVS"), and also samples part of the diluted exhaust gas to introduce the part into an analytical device 10. The exhaust gas sampling apparatus 100 and the analytical device 10 constitute an exhaust gas sampling and analytical system 1.

The exhaust gas sampling apparatus 100 is one that introduces the total amount of the exhaust gas and the dilution gas there into to control a total flow rate of the gases to a constant rate, and introduces the part of the diluted exhaust gas into the analytical device 10 for PM sampling. In addition, the analytical device 10 of the present embodiment is a collection filter for collecting particulate matter (PM) contained in the diluted exhaust gas.

Figure 1:
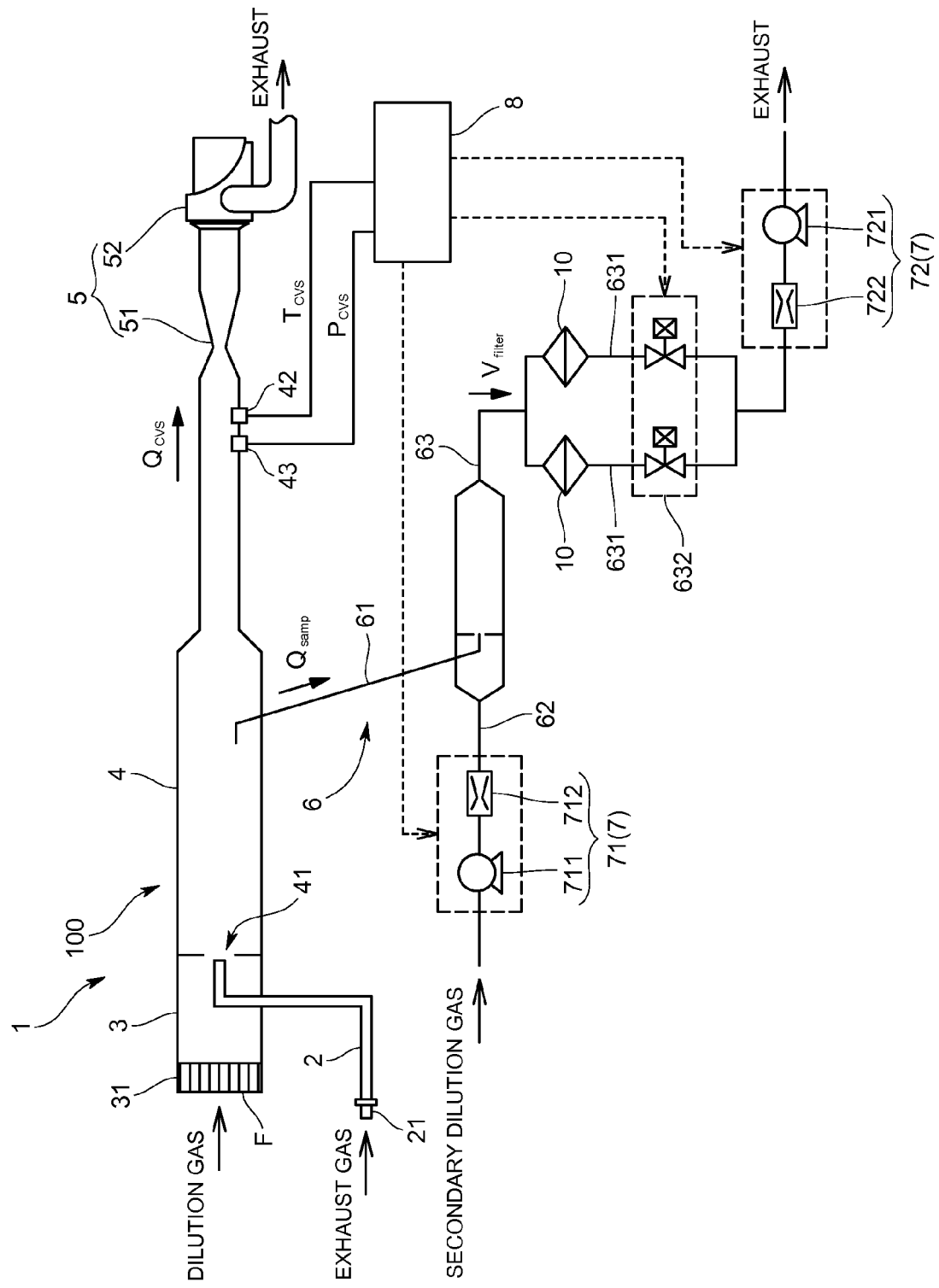
FIG. 1 is a schematic diagram illustrating a configuration of an exhaust gas sampling apparatus of the present embodiment.

Specifically, the exhaust gas sampling apparatus 100 is, as illustrated in FIG. 1, provided with: an exhaust gas flow path 2 through which the exhaust gas flows; a dilution gas flow path 3 through which the dilution gas flows; a main flow path 4 that is connected with the exhaust gas flow path 2 and the dilution gas flow path 3 to flow the diluted exhaust gas that is a mixture of the exhaust gas and the dilution gas; the CVS 5 that is provided in the main flow path 4; a diluted exhaust gas sampling flow path 6 for sampling the part of the diluted exhaust gas from the main flow path 4 to introduce the part into the collection filter 10; a flow rate control mechanism 7 that is provided in the diluted exhaust gas sampling flow path 6 to control a flow rate (Qsamp) of the diluted exhaust gas to be sampled through the diluted exhaust gas sampling flow path 6; and a control device 8 that controls the flow rate control mechanism 7 to set a ratio (split flow ratio) of the flow rate (Qsamp) of the diluted exhaust gas to be sampled through the diluted exhaust gas sampling flow path 6 to a flow rate (QCVS) of the diluted exhaust gas actually flowing through the CVS 5.

The exhaust gas flow path 2 has an exhaust gas introduction port 21 at one end thereof, and is one that from the exhaust gas introduction port 21, receives the total amount of the exhaust gas exhausted from, for example, an exhaust pipe of an automobile.

The dilution gas flow path 3 has a dilution gas introduction port 31 at one end thereof, and is one that introduces air as the dilution gas. Also, the dilution gas introduction port 31 is provided with, for example, an activated carbon filter paper F for removing foreign substances contained in the air. The filter paper F is also intended to stabilize an HC level in the air. Note that the dilution gas introduction port 31 may be provided with a dilution air purification device for removing impurities in the air to supply purified dilution air to the main flow path 4.

The main flow path 4 is connected with the exhaust gas flow path 2 and the dilution gas flow path 3 through a mixing part 41. In addition, the mixing part 41 of the present embodiment is one that is configured by placing an orifice in a pipe.

The CVS 5 provided on a downstream side of the main flow path 4 is configured to include: a venturi 51 provided in the main flow path 4; and a suction pump 52 provided on a downstream side of the venturi 51, such as a turbo blower. In addition, the venturi 51 is a critical flow venturi.

The diluted exhaust gas sampling flow path 6 is one that has a secondary dilution mechanism for further secondarily diluting the diluted exhaust gas, and provided with: a diluted exhaust gas introduction path 61 of which one end is provided in the main flow path 4 to sample the part of the diluted exhaust gas flowing through the main flow path 4; a secondary dilution gas flow path 62 through which secondary dilution gas for further diluting the diluted exhaust gas flows; and a secondarily diluted exhaust gas flow path 63 that is connected with the diluted exhaust gas introduction path 61 and the secondary dilution gas flow path 62 to flow secondarily diluted exhaust gas that is a mixture of the diluted exhaust gas and the secondary dilution gas.

The secondary dilution gas flow path 62 is provided with a flow rate control mechanism 71 for controlling a flow rate of the secondary dilution gas flowing through the secondary dilution gas flow path 62. The flow rate control mechanism 71 is configured to include: a pump 711 that can vary pumping power by controlling a rotation speed; and a flow meter 712 that is provided on a downstream side of the pump 711 to measure the flow rate of the secondary dilution gas, such as a venturi flow meter.

The secondarily diluted exhaust gas flow path 63 has: a plurality of branched flow paths 631 mutually connected in parallel; and a flow path switching mechanism 632 for switching among the branched flow paths 631 such that the diluted exhaust gas (secondarily diluted exhaust gas) flows through one of the plurality of branched flow paths 631, and each of the plurality of branched flow paths 631 is provided with a collection filter 10. The flow path switching mechanism 632 includes solenoid valves provided in the respective branched flow paths 631. ON/OFF of each of the solenoid valves is controlled by an after-mentioned control device 8. In addition, although not illustrated, the secondarily diluted exhaust gas flow path 63 is provided with a bypass flow path not provided with a collection filter 10, and the bypass flow path is also switched by the flow path switching mechanism 632.

Further, in the secondarily diluted exhaust gas flow path 63, a flow rate control mechanism 72 is provided on a downstream side of a meeting point of the branched flow paths 631. The flow rate control mechanism 72 is configured to include: a pump 721 that can vary pump power by controlling a rotation speed; and a flow meter 722 that is provided on an upstream side of the pump 721 to measure a flow rate of the secondarily diluted exhaust gas, such as a venturi flow meter.

In the secondary dilution through the diluted exhaust gas sampling flow path 6 configured as described above, the flow rate control mechanism 71 in the secondary dilution gas flow path 62 and the flow rate control mechanism 72 in the secondarily diluted exhaust gas flow path 63 are controlled by the after-mentioned control device 8 so as to keep a secondary dilution ratio of the secondary dilution always constant. That is, the control device 8 performs the control so as to keep constant the ratio (secondary dilution ratio DR=Qsamp/ (Qsamp+Qsecondary_dilution_gas)) between the flow rate (Qsecondary_dilution_gas) of the secondary dilution gas to flow through the secondary dilution gas flow path 62 and the flow rate (Qsamp) of the diluted exhaust gas to be sampled through the diluted exhaust gas sampling flow path 6.

Next, a specific function of the control device 8 is described.

The control device 8 is one that controls the flow rate control mechanisms 71 and 72 provided in the diluted exhaust gas sampling flow path 6, and thereby controls the split flow ratio (Qsamp/QCVS) of the flow rate (Qsamp) of the diluted exhaust gas to be sampled through the diluted exhaust gas sampling flow path 6 (specifically, the diluted exhaust gas introduction path 61) to the flow rate (QCVS) of the diluted exhaust gas flowing through the CVS 5 to be constant. That is, the control device 8 is one that controls the split flow ratio (Qsamp/QCVS) to be constant as well as controlling the secondary dilution ratio of the diluted exhaust gas to be constant.

Specifically, from a temperature sensor 42 and pressure sensor 43 provided on an upstream side of the CVS 5, the control device 8 obtains values of temperature (TCVS) and pressure (PCVS) of the diluted exhaust gas actually flowing through the CVS 5. Further, the control device 8 uses the diluted exhaust gas temperature (TCVS) and the diluted exhaust gas pressure (PCVS) to calculate the flow rate (QCVS) of the diluted exhaust gas flowing through the CVS 5 according to Expression "QCVS=K×PCVS×TCVS1/2". Here, K is a venturi calibration factor.

Also, in order to make a flow velocity (Vfilter) of the diluted exhaust gas passing through each of the collection filters 10 equal to a predetermined value, the control device 8 calculates the flow rate (Qsamp) of the diluted exhaust gas to be sampled through the diluted exhaust gas sampling flow path 6. Note that the predetermined value refers to, in the present embodiment, a regulated value provided in exhaust gas testing regulations, and for example, the diluted exhaust gas flow velocity is 100 cm/s or less, and close to the value. Also, a flow rate (Qfilter) of the diluted exhaust gas passing through each of the collection filters 10 is a total flow rate that is the sum of the flow rate (Qsecondary_dilution_gas) of the secondary dilution gas flowing through the secondary dilution gas flow path 62 and the flow rate (Qsamp) of the diluted exhaust gas sampled through the diluted exhaust gas sampling flow path 6.

Further, the control device 8 sets the split flow ratio (Qsamp/QCVS) from the diluted exhaust gas flow rate (QCVS) calculated according to the above-described expression and the flow rate (Qsamp) of the diluted exhaust gas to be sampled, which is calculated back from the predetermined diluted exhaust gas flow velocity (Vfilter). As described, the control device 8 controls the flow rate control mechanisms 71 and 72 provided in the diluted exhaust gas sampling flow path 6 so as to meet the set split flow ratio.

Next, the timing to set the split flow ratio in the control device 8 is described.

The control device 8 sets the split flow ratio when the diluted exhaust gas sampling flow path 6 starts to sample the diluted exhaust gas toward any of the collection filters 10. Specifically, the control device 8 sets the split flow ratio every time the flow path switching mechanism 632 switches among the branched flow paths 631.

Figure 2:
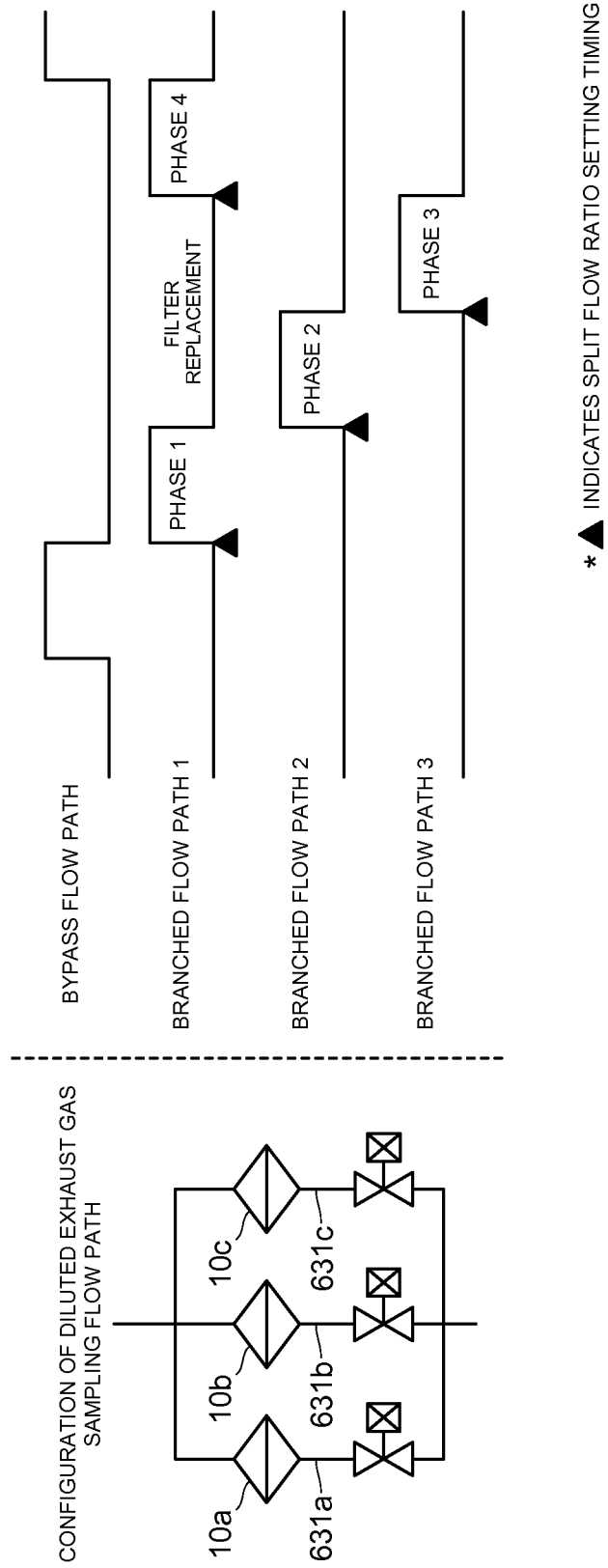
FIG. 2 is a diagram illustrating split flow ratio setting timing in the same embodiment.

In the following, as illustrated in FIG. 2, a configuration in which the diluted exhaust gas sampling flow path 6 has three branched flow paths 631a to 631c, i.e., the case of flowing the diluted exhaust gas sequentially toward three filters 10a to 10c is described. In addition, a phase 1 to a phase 4 described below are running patterns into which a test mode is subdivided, such as a cold start phase, a hot start phase, and a transient phase from the cold start phase to the hot start phase.

When the diluted exhaust gas sampling flow path 6 starts to sample the diluted exhaust gas toward any of the collection filter 10a, i.e., immediately before switching from the bypass flow path to the branched flow path 631 a provided with the first collection filter 10a, the control device 8 obtains the diluted exhaust gas temperature (TCVS) and the diluted exhaust gas pressure (PCVS) respectively from the temperature sensor 42 and the pressure sensor 43 to calculate the diluted exhaust gas flow rate (QCVS). Then, on the basis of the desired flow velocity (Vfilter) of the diluted exhaust gas to be flowed toward the first collection filter 10a, the control device 8 calculates the diluted exhaust gas flow rate (Qsamp) to be sampled, and uses the calculated diluted exhaust gas flow rate (QCVS) and the calculated flow rate (Qsamp) of the diluted exhaust gas to be sampled to set the split flow ratio (Qsamp/QCVS). Subsequently, the control device 8 controls the flow rate control devices 71 and 72 for the first collection filter 10a so as to meet the split flow ratio, and during a predetermined sampling period provided by an exhaust gas test, flows the diluted exhaust gas toward the first collection filter 10a (phase 1).

After the end of the PM sampling at the first collection filter 10a (sampling period), the control device 8 controls the flow path switching mechanism 632 to switch to the branched flow path 631b provided with the second collection filter 10b. Note that immediately before switching from the branched flow path 631a to the branched flow path 631b, the control device 8 obtains the diluted exhaust gas temperature (TCVS) and the diluted exhaust gas pressure (PCVS) respectively from the temperature sensor 42 and the pressure sensor 43 to calculate the diluted exhaust gas flow rate (QCVS). Then, on the basis of the desired flow velocity (Vfilter) of the diluted exhaust gas to be flowed toward the second collection filter 10b, the control device 8 calculates the flow rate (Qsamp) of the diluted exhaust gas to be sampled, and uses the calculated diluted exhaust gas flow rate (QCVS) and the calculated flow rate (Qsamp) of the diluted exhaust gas to be sampled to set the split flow ratio (Qsamp/QCVS). Subsequently, the control device 8 controls the flow rate control devices 71 and 72 for the second collection filter 10b so as to meet the split flow ratio, and during the predetermined sampling period provided by the exhaust gas test, flows the diluted exhaust gas toward the second collection filter 10b (phase 2). Further, switching from the second collection filter 10b to the third collection filter 10c (phase 3) is also made in the same procedure. In addition, FIG. 2 also illustrates the case of, after the end of the PM sampling at the third collection filter 10c, switching to a new first collection filter 10a (phase 4) that has been subjected to filter replacement.

Effects of the Present Embodiment

According to the exhaust gas sampling apparatus 100 of the present embodiment configured as described, the flow rate (QCVS) of the diluted exhaust gas flowing through the CVS 5 is calculated immediately before the PM sampling, and the diluted exhaust gas flow rate (QCVS) is used to set the split flow ratio so as to make the velocity (Vfilter) of the diluted exhaust gas flowing into each of the collection filters 10 equal to the predetermined value, so that in consideration of a temperature-dependent variation in flow rate (QCVS) of the diluted exhaust gas flowing through the CVS 5, the flow velocity (Vfilter) of the diluted exhaust gas flowing into the collection filter 10 can be regulated to the predetermined value.

Also, in the present embodiment, every time switching to each of the collection filters 10 is made, the split flow rate is set immediately before the switching, and therefore the flow velocity (Vfilter) of the diluted exhaust gas flowing into the collection filter 10 can be made as close to the predetermined value such as the regulated value as possible.

Further, in the present embodiment, the diluted exhaust gas sampling flow path 6 has a two-step diluting mechanism, and by diluting the diluted exhaust gas sampled from the main flow path 4 with the secondary dilution gas, temperature of the sampled diluted exhaust gas can be reduced without increasing a piping length of the diluted exhaust gas sampling flow path 6. This enables the exhaust gas sampling apparatus 100 to be compactly configured.

Note that the present invention is not limited to the above-described embodiment.

For example, in the above-described embodiment, in order to make the flow velocity (Vfilter) of the diluted exhaust gas flowing into each of the collection filters 10 equal to the predetermined value, the split flow ratio is set; however, the present invention may be adapted to set the split flow ratio in order to make the flow rate (Qfilter) of the diluted exhaust gas flowing into each of the collection filters 10 equal to a predetermined value. Note that in the case of the above-described embodiment, the flow rate (Qfilter) of the diluted exhaust gas flowing into each of the collection filters 10 is the total flow rate that is the sum of the flow rate (Qsamp) of the sampled diluted exhaust gas and the flow rate (Qsecondary_dilution_gas) of the secondary dilution gas.

Figure 3:
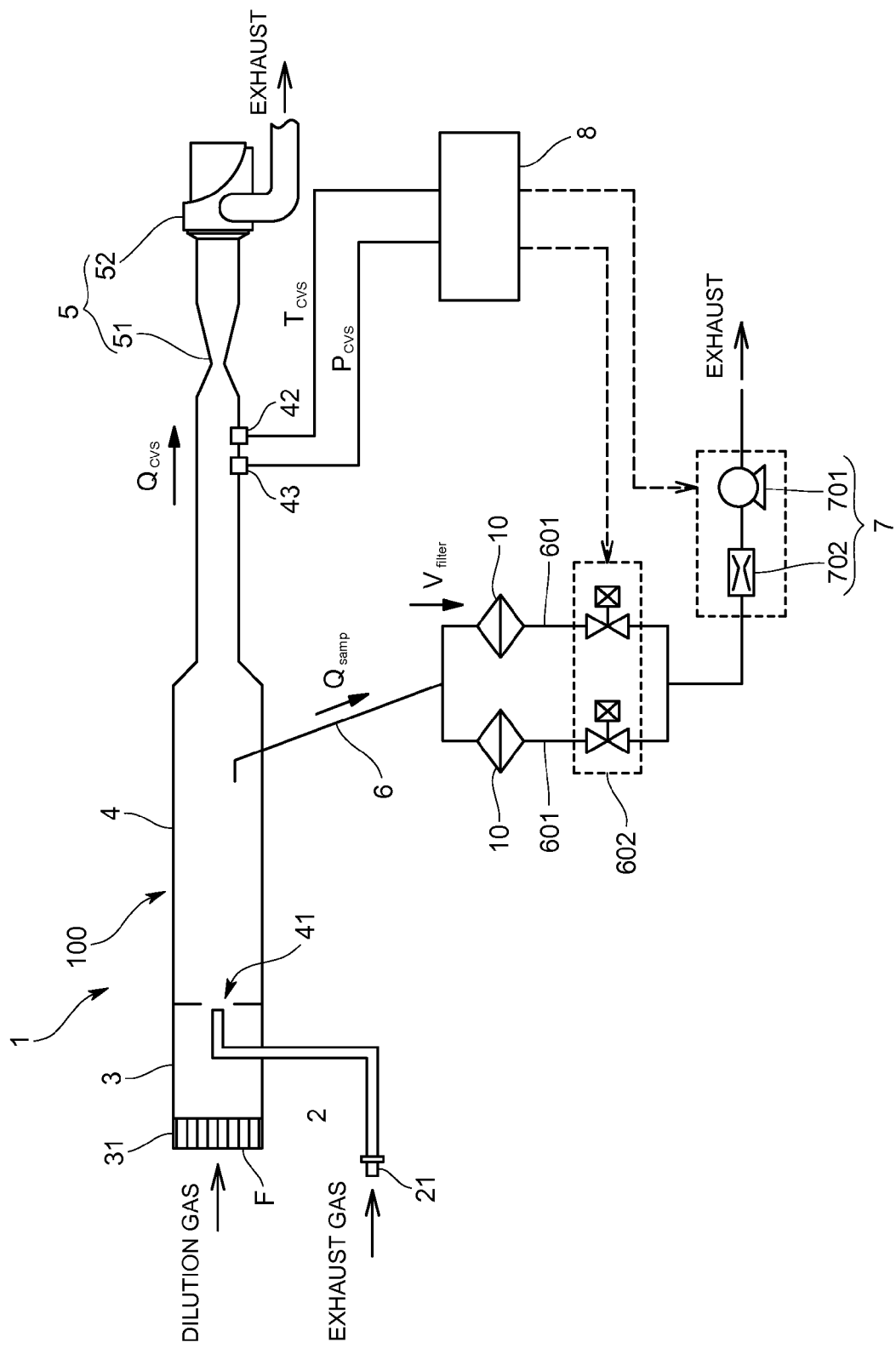
FIG. 3 is a schematic diagram illustrating an exhaust gas sampling apparatus of a variation.

Also, the present invention may be adapted such that the diluted exhaust gas sampling flow path 6 does not have the two-step diluting mechanism. Specifically, as illustrated in FIG. 3, a diluted exhaust gas sampling flow path 6 has: a plurality of branched flow paths 601 mutually connected in parallel; and a flow path switching mechanism 602 for switching among the branched flow paths 601 such that diluted exhaust gas flows through one of the plurality of branched flow paths 601, and each of the plurality of branched flow paths 601 is provided with a collection filter 10. Further, in the diluted exhaust gas sampling flow path 6, a flow rate control mechanism 7 is provided on a downstream side of a meeting point of the branched flow paths 601. The flow rate control mechanism 7 is, as in the above-described embodiment, configured to include: a pump 701 that can vary pumping power by controlling a rotation speed; and a flow meter 702 that is provided on an upstream side of the pump 701 to measure a flow rate of the diluted exhaust gas, such as a venturi flow meter.

Figure 4:
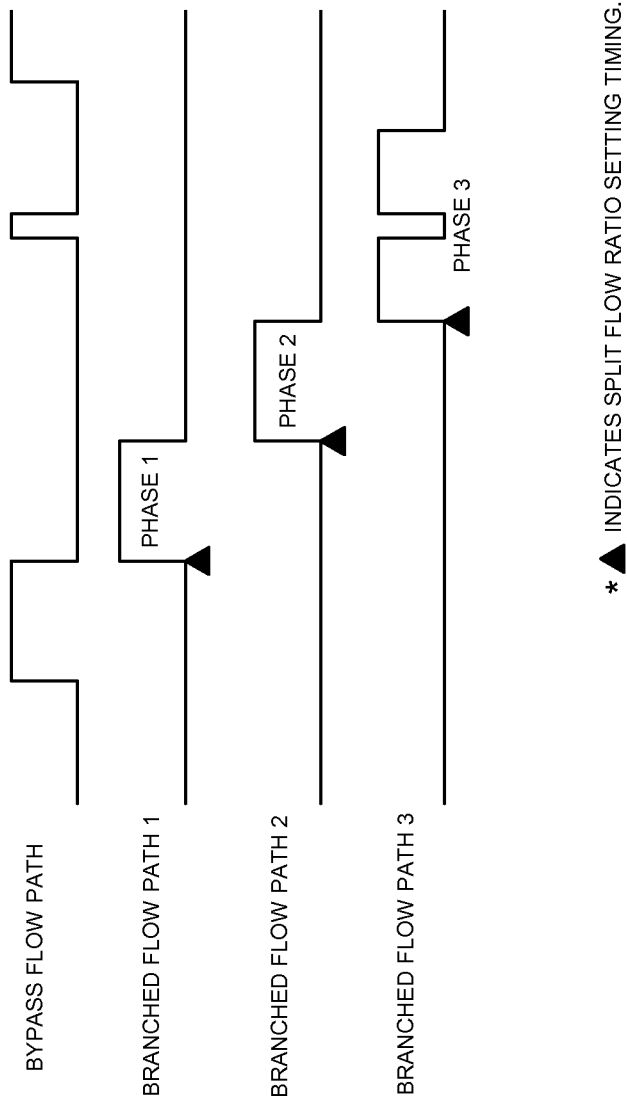
FIG. 4 is a diagram illustrating a variation of the split flow ratio setting timing.
Figure 5:
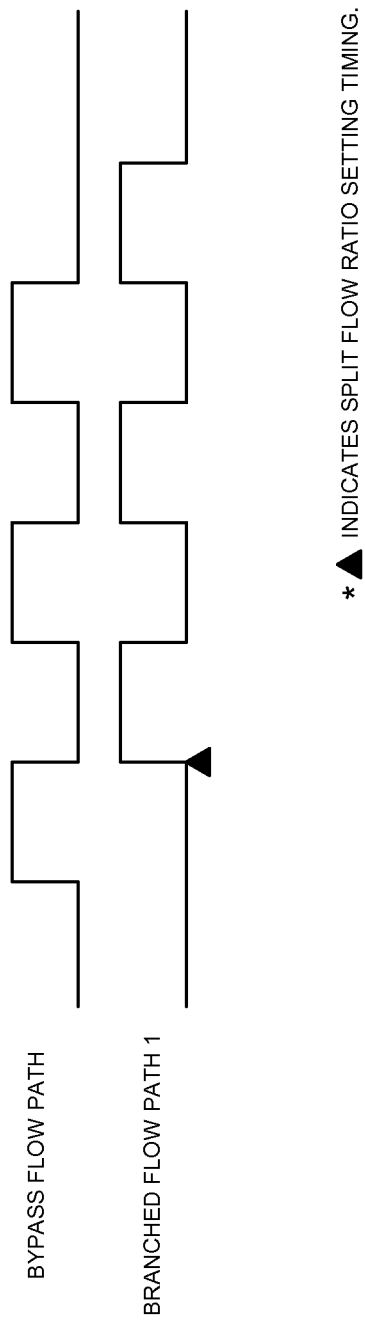
FIG. 5 is a diagram illustrating another variation of the split flow ratio setting timing.

Still further, the timing to set the split flow ratio may be, in addition to that in the above-described embodiment, determined as in FIG. 4 or 5. FIG. 4 or 5 illustrates the setting timing in the case of intermittently flowing the diluted exhaust gas toward the same collection filter 10. That is, in the case of intermittently flowing the diluted exhaust gas toward the same collection filter 10 (in FIG. 4, the collection filter 10c), the diluted exhaust gas is sampled at a split flow ratio initially set for the collection filter 10 without changing the split flow ratio, and the sampled diluted exhaust gas is flowed toward the collection filter 10.

Figure 6:
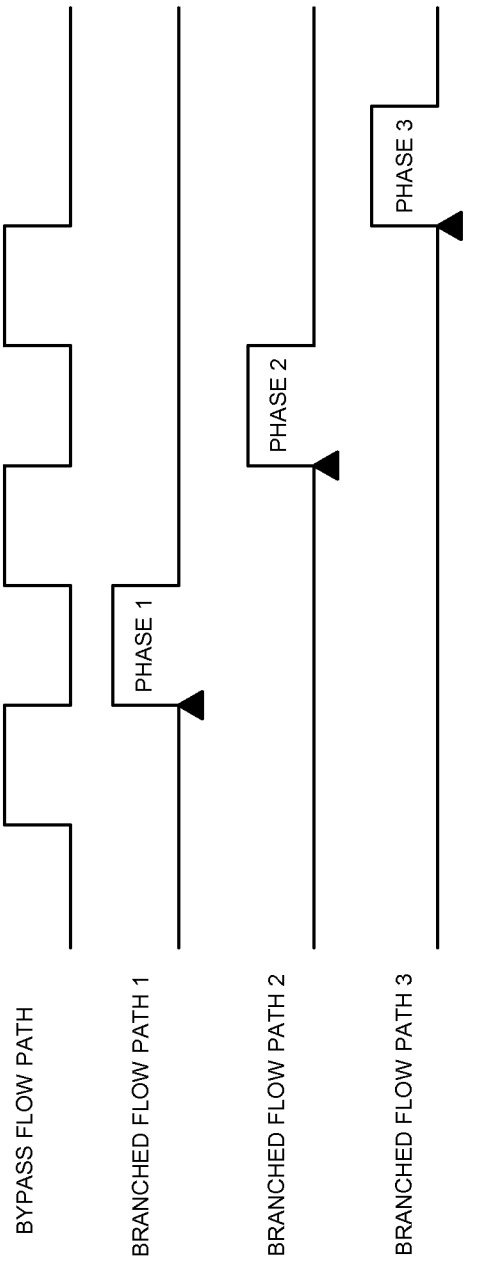
FIG. 6 is a diagram illustrating still another variation of a branched flow path switching method and the split flow ratio setting timing.

In addition, the switching among the plurality of branched flow paths is not continuously made, but as illustrated in FIG. 6, may be made so as to switch to a next branched flow path through switching to the bypass flow path. In this case, the split flow ratio setting timing is the time to switch from the bypass flow path to each of the branched flow paths or the time immediately before the switching.

In the case of switching between the bypass flow path and a single branched flow path, the split flow ratio setting timing may be the time to switch from the bypass flow path to the branched flow path or the time immediately before the switching.

The above-described embodiment is adapted to, from the temperature sensor and pressure sensor provided on the upstream side of the CVS, respectively obtain the diluted exhaust gas temperature (TCVS) and diluted exhaust gas pressure (PCVS) to calculate the diluted exhaust gas flow rate (QCVS); however, the present invention may be configured as follows.

That is, before a final test where the exhaust gas sampling is performed, an automobile is preliminarily run in the same manner as that in the final test, and a temperature change in diluted exhaust gas temperature obtained from the temperature sensor at the time of the preliminary running is stored in the control device 8. Then, in the final test where the exhaust gas sampling is performed, the control device sets a split flow ratio for each of the phases on the basis of the temperature change obtained at the time of the preliminary running Specifically, the control device 8 uses the lowest diluted exhaust gas temperature among temperatures in the respective phases to calculate the diluted exhaust gas flow rate (QCVS). Note that the present invention may be adapted such that, in addition to the temperature change, or in place of the temperature change, a pressure change of the diluted exhaust gas is stored in the control device 8, and the pressure change is used to calculate the diluted exhaust gas flow rate (QCVS).

Further, the above-described embodiment is adapted to use each of the collection filters as the analytical device; however, the analytical device may be a sampling bag for sampling a predetermined amount of diluted exhaust gas, or may be a gas analyzer for measuring the concentration of a predetermined component contained in the diluted exhaust gas.

In addition, the exhaust gas sampling apparatus may be one that, with dilution gas, dilutes engine exhaust gas exhausted from a gasoline engine mounted in, for example, an automobile or the like, and sucks the diluted exhaust gas by the CVS as well as sampling part of the diluted exhaust gas to introduce the part into the analytical device 10.

Besides, it should be appreciated that the present invention is not limited to any of the above-described embodiments, but can be variously modified without departing from the scope thereof.

REFERENCE SIGNS LIST

100: Exhaust gas sampling apparatus
10: Collection filter (analytical device)
2: Exhaust gas flow path
3: Dilution gas flow path
4: Main flow path
5: Constant volume sampler (CVS)
6: Diluted exhaust gas sampling flow path
631: Branched flow path
632: Flow path switching mechanism
7: Flow rate control mechanism
8: Control device

What is claimed is:
1. An exhaust gas sampling apparatus comprising:
an exhaust gas flow path through which exhaust gas flows;
a dilution gas flow path through which dilution gas flows;
a main flow path that is connected with the exhaust gas flow path and the dilution gas flow path to flow diluted exhaust gas that is a mixture of the exhaust gas and the dilution gas;
a constant volume sampler that is provided in the main flow path;
a temperature sensor that is provided in the main flow path upstream of the constant volume sampler;
a diluted exhaust gas sampling flow path for sampling part of the diluted exhaust gas from the main flow path to introduce the part into a collection filter for collecting particulate matter contained in the diluted exhaust gas;
a flow rate control mechanism that is provided in the diluted exhaust gas sampling flow path to control a flow rate of the diluted exhaust gas to be sampled through the diluted exhaust gas sampling flow path; and
a control device that controls the flow rate control mechanism to set a ratio of the flow rate of the diluted exhaust gas to be sampled through the diluted exhaust gas sampling flow path to a flow rate of the diluted exhaust gas flowing through the constant volume sampler, wherein
the control device obtains values of temperature of the diluted exhaust gas flowing through the constant volume sampler from the temperature sensor, calculates the flow rate of the diluted exhaust gas flowing through the constant volume sampler by using the temperature, and sets the ratio so as to make the flow rate of the diluted exhaust gas flowing into the collection filter equal to a predetermined value.

2. The exhaust gas sampling apparatus according to claim 1, wherein
the control device sets the ratio at a start of sampling the diluted exhaust gas through the diluted exhaust gas sampling flow path.

3. The exhaust gas sampling apparatus according to claim 1, wherein
the control device sets the ratio every time a test mode is switched, or every time a phase provided in each test mode is switched.

4. An exhaust gas sampling and analytical system using the exhaust gas sampling apparatus according to claim 1, the exhaust gas sampling and analytical system further comprising a sampling bag for sampling a predetermined amount of diluted exhaust gas, or a gas analyzer for measuring the concentration of a predetermined component contained in the diluted exhaust gas.

* * * * *